United States Patent
Knight

(10) Patent No.: US 10,443,935 B2
(45) Date of Patent: Oct. 15, 2019

(54) APPARATUS FOR MAINTAINING A CONTROLLED ENVIRONMENT

(71) Applicant: GEN-PROBE INCORPORATED, San Diego, CA (US)

(72) Inventor: Byron J. Knight, San Diego, CA (US)

(73) Assignee: Gen-Probe Incorporated, San Diego, CA (US)

( * ) Notice: Subject to any disclaimer, the term of this patent is extended or adjusted under 35 U.S.C. 154(b) by 51 days.

(21) Appl. No.: 15/745,834

(22) PCT Filed: Aug. 2, 2016

(86) PCT No.: PCT/US2016/045166
§ 371 (c)(1),
(2) Date: Jan. 18, 2018

(87) PCT Pub. No.: WO2017/023934
PCT Pub. Date: Feb. 9, 2017

(65) Prior Publication Data
US 2018/0209731 A1 Jul. 26, 2018

Related U.S. Application Data

(60) Provisional application No. 62/200,370, filed on Aug. 3, 2015.

(51) Int. Cl.
*F26B 5/06* (2006.01)
*A01N 1/02* (2006.01)
(Continued)

(52) U.S. Cl.
CPC .............. *F26B 5/06* (2013.01); *A01N 1/0252* (2013.01); *A01N 1/0289* (2013.01); *B01L 1/02* (2013.01);
(Continued)

(58) Field of Classification Search
CPC ........ F26B 5/06; F26B 25/063; A01N 1/0252; A01N 1/0289; B01L 1/02; B01L 7/00; B01L 9/06; B01L 2200/0689
(Continued)

(56) References Cited

U.S. PATENT DOCUMENTS 8,528,225 B2 * 9/2013 Weisselberg .............. F26B 5/00
34/284
8,875,413 B2 * 11/2014 Ling .................. F26B 5/06
34/298
(Continued)

FOREIGN PATENT DOCUMENTS

CN 101726584 A 6/2010
CN 104081142 A 10/2014
(Continued)

OTHER PUBLICATIONS

International Preliminary Report on Patentability dated Feb. 6, 2018 issued in International Application No. PCT/US2016/045166. (8 pages).
(Continued)

*Primary Examiner* — Stephen M Gravini
(74) *Attorney, Agent, or Firm* — Rothwell, Figg, Ernst & Manbeck, P.C.; Jeffrey Landes, Esq.

(57) ABSTRACT

A lyophilization nest and method of using the same is described herein. In various embodiments, the lyophilization nest is configured to support one or more receptacles each supporting one or more substances within an interior space of the lyophilization nest. The interior space may be in fluid communication with the exterior of the lyophilization nest through one or more vent holes extending through a surface of the lyophilization nest. Each of the one or more vent holes have a corresponding sealing element configured to selectively form an air-tight seal within the vent holes, such that a controlled environment may be maintained within the
(Continued)

interior space when the ambient conditions surrounding the lyophilization nest are not lyophilization conditions. The one or more sealing elements may be operable while the lyophilization nest is positioned within a sealed lyophilizer by depressing the sealing elements into corresponding vent holes to form the air-tight seal.

18 Claims, 9 Drawing Sheets

(51) Int. Cl.
    *B01L 9/06*         (2006.01)
    *F26B 25/06*       (2006.01)
    *B01L 7/00*         (2006.01)
    *B01L 1/02*         (2006.01)

(52) U.S. Cl.
    CPC .................. *B01L 7/00* (2013.01); *B01L 9/06* (2013.01); *F26B 25/063* (2013.01); *B01L 2200/0689* (2013.01); *B01L 2300/042* (2013.01); *B01L 2300/0829* (2013.01); *B01L 2300/1894* (2013.01); *B01L 2400/049* (2013.01)

(58) Field of Classification Search
    USPC .......................................................... 34/284
    See application file for complete search history.

(56) References Cited

U.S. PATENT DOCUMENTS

| | | | | |
|---|---|---|---|---|
| 8,919,007 B2* | 12/2014 | Friess | ....................... | F26B 5/06 34/90 |
| 9,003,676 B2* | 4/2015 | Yarborough | .......... | A61M 5/002 34/287 |
| 9,278,790 B2* | 3/2016 | McPherson | ............... | F26B 5/06 |
| 9,823,018 B2* | 11/2017 | Parker | ..................... | F26B 5/044 |
| 9,828,124 B2* | 11/2017 | Wissner | ................... | F26B 5/06 |
| 9,863,699 B2* | 1/2018 | Corbin, III | ................ | F26B 5/06 |
| 9,945,611 B2* | 4/2018 | DeMarco | ............... | F26B 5/065 |
| 10,139,162 B2* | 11/2018 | Plavnik | ..................... | F26B 7/00 |
| 2001/0001348 A1 | 5/2001 | Wisniewski | | |
| 2010/0101106 A1 | 4/2010 | Kim et al. | | |
| 2011/0154682 A1 | 6/2011 | Kuu et al. | | |
| 2014/0259724 A1 | 9/2014 | McCarthy et al. | | |
| 2018/0023893 A1* | 1/2018 | Schuetz | ................... | F26B 5/06 34/287 |
| 2018/0209731 A1* | 7/2018 | Knight | ...................... | B01L 7/00 |
| 2019/0001324 A1* | 1/2019 | Knight | ................ | B01L 3/50825 |

FOREIGN PATENT DOCUMENTS

| | | | | |
|---|---|---|---|---|
| CN | 105050636 A | | 11/2015 | |
| EP | 0 413 620 A1 | | 2/1991 | |
| EP | 0413620 B1 | * | 1/1994 | .......... B65B 31/027 |
| EP | 909719 A1 | * | 4/1999 | |
| GB | 792071 A | * | 3/1958 | ............ G01T 1/202 |
| JP | 2001106242 A | | 4/2001 | |
| JP | 2016205850 A | * | 12/2016 | |
| WO | 00/44641 A2 | | 8/2000 | |
| WO | WO-2017023934 A1 | * | 2/2017 | ................ B01L 7/00 |

OTHER PUBLICATIONS

EPO Communication pursuant to Article 94(3) EPC, European Application No. 16756832.8, Nov. 14, 2018.
International Search Report and Written Opinion issued in International Patent Application No. PCT/US2016/045166, 12 pages (dated Nov. 9, 2016).
First Office Action dated Apr. 11, 2019 issued in Chinese Patent Application No. 201680046000.2. (12 pages).
Chinese Search Report dated Apr. 11, 2019 issued in Chinese Patent Application No. 201680046000.2 (6 pages).

* cited by examiner

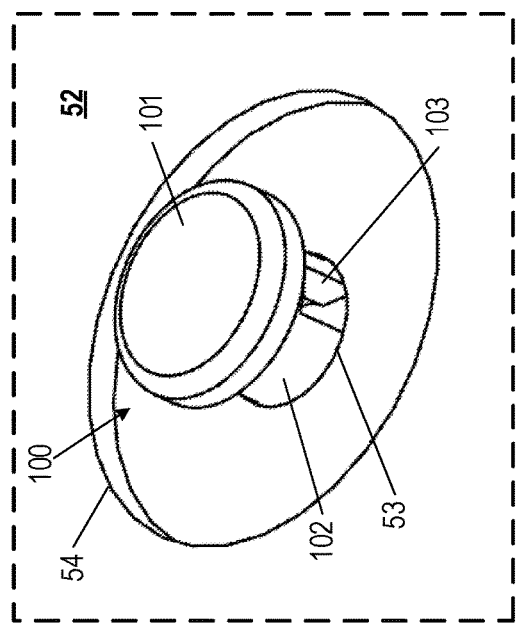
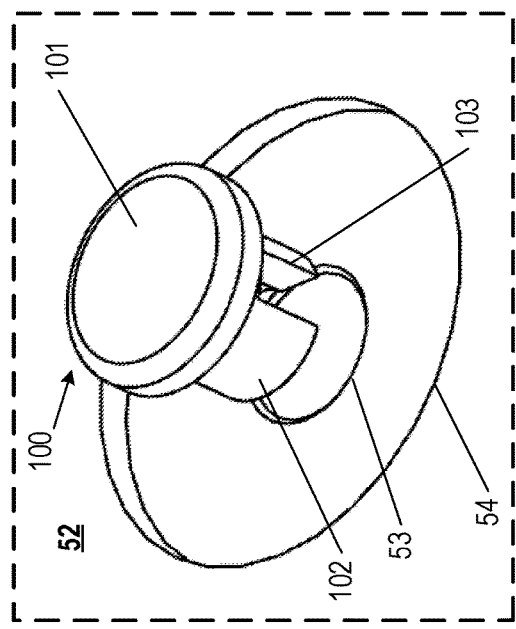
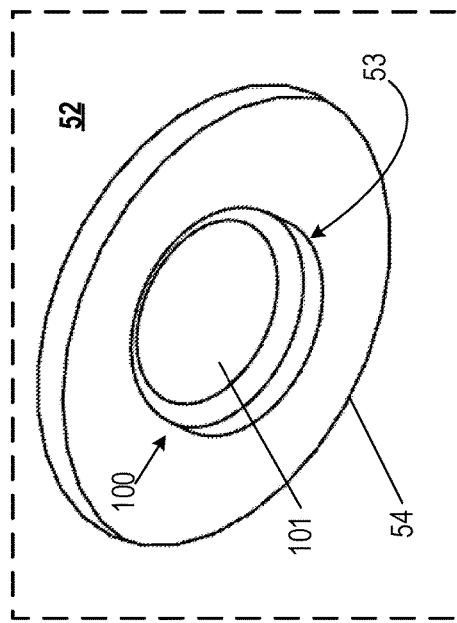

APPARATUS FOR MAINTAINING A CONTROLLED ENVIRONMENT

CROSS-REFERENCE TO RELATED APPLICATION

This application is a 35 U.S.C. 371 National Phase Entry Application from PCT/US2016/045166, filed Aug. 2, 2016, which claims the benefit under 35 U.S.C. § 119(a) of the filing date of U.S. Provisional Application No. 62/200,370, filed Aug. 3, 2015, the respective disclosures which are incorporated herein by reference.

BACKGROUND

Lyophilization is a process used to remove water from substances allowing these substances to be stored for longer periods of time without material deterioration. Typically these substances are of biological or synthetic origin and may include antibiotics, pharmaceuticals, chemicals, sera, vaccines, cells, tissues, protein and/or nucleic acids.

Substances can be lyophilized by placing individual vials or a multi-well plate containing one or more substances into a lyophilizer, which generates and maintains a controlled environment therein during the lyophilization process. The environmental factors that are controlled by the lyophilizer include, but are not limited to, temperature, air pressure/vacuum level, humidity, and/or gas content. After lyophilization is complete, the seal on the lyophilizer is released, and consequently the controlled environment within the lyophilizer is diluted with the air surrounding the lyophilizer, which can be detrimental to lyophilized substances. A primary consequence of contacting lyophilized substances with the air from outside of the lyophilizer is that the air generally contains moisture (e.g., water vapor) which may rehydrate (at least partially) the lyophilized substances. Depending on factors such as the time of year, the room air-conditioning, the number of people in a room and the exposure time, lyophilized substances in contact with air from outside of the lyophilizer can undergo from 40% to 70% rehydration. Introducing moisture to the lyophilized substances can negatively affect the stability of the substances. If the substances are not going to be used immediately, the vials and/or wells of the multi-well plates can be sealed by placing a foil or other sealing material over the wells and/or vials, thereby sealing and isolating the lyophilized substances from the air. The seal provides a barrier between environmental conditions surrounding the plate and the substances located within each vial or well of the plate after the plate has been removed from the lyophilizer. Thus, the seal impedes rehydration of substances that results from absorbing water vapor from the atmosphere. The sealed vials and/or plates containing the one or more substances can then be stored or sold in commerce for later use. The seals can then be broken such that the stored substances within one or more of the vials and/or individual wells may be accessed during use.

The process of sealing receptacles after removal from the lyophilizer exposes the individual substances to unfavorable environmental conditions during the period of time between removal of the receptacle from the lyophilizer until the receptacle is sealed. While this exposure time can vary depending on the number of vials and/or wells of the multi-well plate to be sealed, the number of technicians available to seal the vials and/or wells, the transportation distance between the lyophilizer and the sealing station, and other factors experienced during a lyophilization procedure, the exposure time for lyophilized substances in a high-production facility may be between 4-5 hours. As a result, the lyophilized substances in each vial or well of the multi-well plate may be exposed to uncontrolled and potentially unfavorable environmental conditions, including moisture, prior to being sealed.

Prolonged exposure of the lyophilized substances to these uncontrolled environmental conditions during the period of time between removal of receptacles from the lyophilizer until the receptacles are sealed may be reduced by placing the receptacles into a glovebox (e.g., the Purelab HE 4GB 2500 Glovebox, available from Innovating Technology, Inc. Newburyport, Mass.) immediately after removal from the lyophilizer within which an operator may seal each of the receptacles. However, manipulation of the receptacles may be cumbersome when using a glove box. Additionally, the moisture vapor exposure time during transfer of the receptacles from the lyophilizer to the glovebox may still be significant and may lead to moisture absorption by the lyophilized substances. Furthermore, the environment within a glovebox cannot be made the same as the environment within the lyophilizer itself, and so the lyophilized substances remains exposed to an unfavorable humidity level for a long period of time before being sealed.

A lyophilizer may be operated within a dry room with low humidity. On removal of receptacles from the lyophilizer, substances are exposed only to the dry room prior to sealing. However, dry rooms require precision climate control systems for maintaining low humidity within a room-volume sized to accommodate at least one operator. The humidity levels are again not the same as those within the lyophilizer, though, and the mere presence of an operator within the dry room further negatively impacts the environmental conditions. Dry rooms are expensive to maintain, subject to contamination, and cumbersome to operate because conditions may be hazardous for individuals working inside of these rooms, and accordingly the amount of time an individual may work within these rooms may be limited.

Large stoppered individual vials storing a single substance can be configured for the stoppers to engage while the individual vials are located within a sealed lyophilizer However, such individual vials are difficult to manage, bulky to store, and not usually compatible with laboratory equipment designed for handling samples in a multi-well format.

BRIEF SUMMARY

Described herein a lyophilization nest for preparing lyophilized substances, comprising: a base comprising a bottom plate having a base edge extending upwardly from a perimeter thereof, the bottom plate having a top surface adapted to support a single receptacle or a plurality of receptacles thereon; a cover comprising a top plate having a cover edge extending downwardly from a perimeter thereof, the top plate having one or more vent holes extending therethrough; an interior space defined by the base and the cover when the base and the cover are in the closed relationship, a gasket situated between the base edge and the cover edge and forming an air tight seal between the base edge and the cover edge when compressed; one or more sealing elements, each of the sealing elements being in closeable engagement (e.g., sliding engagement, hinging engagement, swinging engagement, rotary engagement, and the like) with a corresponding one of the vent holes, such that the sealing elements and the corresponding vent holes are operable between: (i) an open configuration in which the positions of the sealing elements relative to the corresponding vent holes permit fluid communication between the interior space and the air outside of the lyophilization nest when the base and the cover are in the closed relationship; and (ii) a closed configuration in which the positions of the sealing elements relative to the corresponding vent holes do not permit fluid communication between the interior space and the air outside of the lyophilization nest when the base and the cover are in the closed relationship, such that the interior space is sealed off to air external the lyophilization nest when the base and the cover are in the closed relationship.

In various embodiments, each of the one or more sealing elements is a flexible plug that comprises a sealing cap and a body portion depending therefrom, the body portion being in a sliding closeable engagement with a corresponding one of the vent holes and having one or more vent slots formed therein. Each of the sealing elements is configured to be positioned in a corresponding vent hole, such that (i) the interior space is in fluid communication with the air outside of the lyophilization nest via the vent slots when the sealing element and the corresponding vent hole are in the open configuration; and (ii) the interior space is not in fluid communication with the air outside of the lyophilization nest when a bottom surface of the sealing cap is in sealing contact with a top surface of the top plate when the sealing element and the corresponding vent hole are in the closed configuration.

In various embodiments, at least one of the base and the cover comprise aluminum. Various embodiments may comprise a hinge along one or more edges of the top plate or the base to provide a clamshell configuration between the base and the cover.

In various embodiments, the base interior is configured to support one or more receptacles therein. In various embodiments, the receptacles may each comprise a plurality of lyophilization wells configured to be sealed and a plastic and/or low moisture vapor transmission rate material, such as a cyclic olefin copolymer. Moreover, in various embodiments, the top surface of the bottom plate comprises one or more receptacle receiving portions formed thereon, each of the receptacle receiving portions having features that conform to at least a bottom end of the one or more receptacles to be received thereon and are constructed to conduct heat between the base and the one or more receptacles supported thereon. In various embodiments, each of the one or more receptacles to be supported within the lyophilization nest comprise a plurality of lyophilization wells, and each of the receptacle receiving portions comprises a plurality of well receiving features conforming to the shapes of at least the bottom ends of lyophilization wells of the corresponding receptacle. Moreover, in various embodiments, the lyophilization nest additionally comprises one or more receptacle frames situated on a top surface of the bottom plate, each receptacle frame configured to support a plurality of receptacles (e.g., four receptacles).

In various embodiments the lyophilization nest further comprises one or more fasteners for securing the cover to the base. The fasteners of the lyophilization nest are configured to compress the gasket between the base edge and the cover edge to form the air tight seal when the base and the cover are in the closed relationship. As an example, the fastener further comprises a base engagement member such as a base pin, a cover engagement member such as a cam lever, and a linking member that links the other two members. As further examples, the fastener can be a latch, a bolt, a clamp, or other structure that compresses the gasket between the base edge and the cover edge to form the air tight seal when the base and the cover are in the closed relationship.

Various embodiments herein are directed to a lyophilization system for lyophilizing one or more substances, the lyophilization system comprising: a sealable enclosure defining a chamber and having a plurality of shelves. In various embodiments, the plurality of shelves are a top shelf and a bottom shelf contained within the chamber. In various embodiments, the plurality of shelves are at least one top shelf and at least one bottom shelf. In various embodiments, the plurality of shelves are a top shelf, a bottom shelf and at least one middle shelf that can be referred to as a top shelf and/or bottom shelf depending on its spatial relationship to a lyophilization nest in the lyophilization system. In various embodiments, the plurality of shelves are a top shelf, a bottom shelf and at least two middle shelves that can be referred to as a top shelf and/or bottom shelf depending on their spatial relationship to a lyophilization nest in the lyophilization system. In various embodiments, the plurality of shelves are at least one top shelf and at least one bottom shelf, each relative to a lyophilization nest in the lyophilization system. In various embodiments, a lyophilization nest is situated on a bottom shelf. In various embodiments, at least one of a top shelf and a bottom shelf is capable of an automated movement that causes the top shelf to engage the sealing elements, thereby altering the sealing elements and the corresponding vent holes from the open configuration to the closed configuration. In various embodiments, the top shelf is positioned above the lyophilization nest and is configured for automated downward movement toward a top surface of the cover of the lyophilization nest.

Various embodiments herein are directed to a lyophilization system for lyophilizing one or more substances, the lyophilization system comprising: a sealable enclosure defining a chamber and having at least one top shelf and at least one bottom shelf contained within the chamber; and at least one lyophilization nest situated on a bottom shelf. In various embodiments, at least one of a top shelf and a bottom shelf is capable of an automated movement that causes the top shelf to engage the sealing elements of the lyophilization nest(s) on the shelf below (bottom shelf), thereby altering the sealing elements and the corresponding vent holes from the open configuration to the closed configuration. In various embodiments, the top shelf is positioned above the lyophilization nest(s) and is configured for automated downward movement toward a top surface of the cover of the lyophilization nest(s). Various embodiments are directed to a method for lyophilizing one or more substances, comprising positioning a lyophilization nest on a bottom shelf contained within a chamber of a lyophilizer, wherein the lyophilization nest is supporting one or more receptacles within an interior space of the lyophilization nest, and at least one of the receptacles contains one or more substances to be lyophilized. The interior of the closed lyophilization nest is in fluid communication with the air outside of the lyophilization nest through one or more vent holes extending through a top plate of a cover of the lyophilization nest and having a sealing element in sliding engagement therewith. The method additionally comprises steps for closing the chamber containing the lyophilization nest, creating a controlled environment having lyophilization conditions within the chamber for a period of time sufficient for the substance(s) contained in the receptacles to be lyophilized. Moreover, the method may comprise causing at least one of a bottom shelf and a top shelf contained within the chamber to move so that the top shelf engages the sealing elements, thereby closing the vent holes so that the interior space of the lyophilization nest is sealed off from the air outside of the lyophilization nest. The sealed lyophilization nest contains within the interior space, the environmental conditions from the sealed lyophilization chamber, which includes a low moisture content, and may further include other factors from the environment of the sealed chamber such as nitrogen gas. The sealed lyophilization nest is no longer in fluid communication with the sealed chamber. Thus the chamber can be unsealed, which results in the introduction of environmental conditions that are typically unfavorable to maintaining the lyophilized substance(s), without exposing the lyophilized substance(s) within the sealed lyophilization nests to the unfavorable environmental conditions.

In various embodiments, creating within a lyophilization chamber a controlled environment for lyophilization comprises generating a vacuum and cycling between temperatures below freezing, which will dry the substance(s) within the chamber. At the end of these steps in the lyophilization process, the humidity level is near zero. In order to unseal the lyophilization chamber, the vacuum must first be released. The vacuum is preferably released by flooding the chamber with nitrogen gas. A high nitrogen environment is preferred because of its low moisture content. It is preferred that the lyophilization nest is sealed following the introduction of nitrogen into the chamber, thereby sealing into the interior of the lyophilization nest a high nitrogen environment. However, this is not mandatory, and the lyophilization nest can be sealed any time following drying of the substances within. Once the vacuum has been released, the chamber door can be opened.

In various embodiments, the method may additionally comprise accessing and removing the receptacles from the lyophilization nest, and sealing the receptacles so as to form an air tight seal between each of a plurality of wells of each of the receptacles, thereby isolating the interior of the wells from environmental conditions that negatively impact a lyophilized substance in the well. In various embodiments, the receptacle is sealed by securing a low moisture vapor transmission film, such as, a laminate structure comprising a layer of aluminum foil to a top surface of each of the receptacles to thereby form the airtight seal between the wells and the air exterior the sealed wells.

In various embodiments, the relative humidity within the interior space of the lyophilization nest remains at 10%, more preferably at less than 10%, more preferably at less than 5%, more preferably at approximately 0% relative humidity for at least four hours, or for at least 8 hours, or for an amount of time from four hours to eight hours. In various embodiments, the absolute humidity within the interior space of the lyophilization nest remains at 2.3 grams of water per cubic meter of air, more preferably at less than 2.3 grams of water per cubic meter of air, more preferably at less than 1.15 grams of water per cubic meter of air, more preferably at less than 0.23 grams of water per cubic meter of air, more preferably at approximately at 0.0 grams of water per cubic meter of air for at least four hours, or for at least eight hours, or for a time period from four hours to eight hours.

BRIEF DESCRIPTION OF THE SEVERAL VIEWS OF THE DRAWINGS

Reference will now be made to the accompanying drawings, which are not necessarily drawn to scale, and wherein:

FIGS. 4A-4C show various positions of a sealing element within a vent hole according to one embodiment;

FIGS. 7-9 also illustrate a chamber comprising a top shelf and a bottom shelf shown in various positions external the cover and base of the nest.

DETAILED DESCRIPTION

Figure 1:
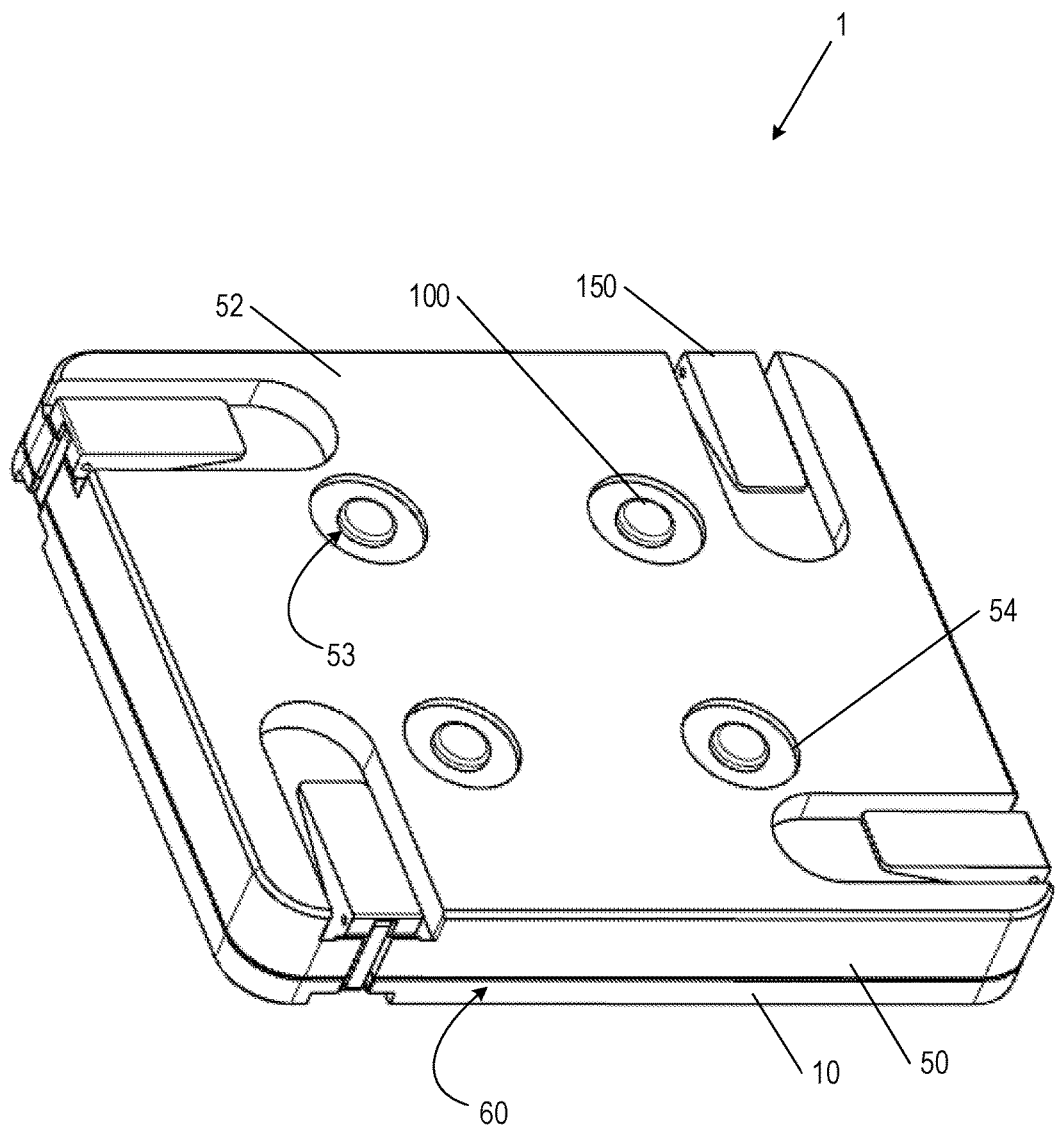
FIG. 1 shows a lyophilization nest in a sealed configuration according to one embodiment.

The lyophilization nest will now be described more fully hereinafter with reference to the accompanying drawings, in which some, but not all embodiments of the nest are shown. Indeed, the lyophilization nest may be embodied in many different forms and should not be construed as limited to the embodiments set forth herein. Rather, these embodiments are provided so that this disclosure will satisfy applicable legal requirements. Like numbers refer to like elements throughout.

Lyophilization is a well-known process for drying a substance so to preserve that substance. The primary mechanism that allows for lyophilization is sublimation, whereby ice is directly converted to water vapor, without passing through the intermediary stage of a liquid. Rather than through heating, this is done by removal of pressure so that the ice boils without melting. The result is a substance whose structure is largely preserved, which has a negligible water content, and which can be stored at room temperatures and pressures. In order to lyophilize a substance, a number of factors of the environment surrounding the substance are altered compared to the more typical levels for these factors in the environment. A number of environmental factors are frequently altered during a lyophilization reaction, including one or more of temperature, air pressure, atmospheric gas content, and humidity. Those skilled in the art of lyophilization will readily develop and implement a set of environmental conditions to achieve lyophilization of a substance of interest. The term "controlled environment" and various forms thereof are used herein in reference to the an environment wherein a number of the factors are altered in order to lyophilize a substance or to maintain a low water content in a substance that has been lyophilized As used herein, an "uncontrolled environment" and related terms refers to an environment with factors that are unfavorable to lyophilization of a substance or to maintaining a low water content in a substance that has been lyophilized. It is noted that uncontrolled environment is not being used herein to indicate that an environment is not controlled in some manner (e.g., room air conditioning and the like), but rather is being used herein to conveniently refer to environmental conditions that are unfavorable towards lyophilizing a substance and maintaining low water content in the substance following lyophilization.

Various embodiments are directed to a lyophilization nest configured to maintain a controlled environment having at least a low humidity level around one or more substances after completion of a lyophilization process using a lyophilization system. The lyophilization system, comprising a lyophilizer, a lyophilization nest, and one or more receptacles each containing one or more substances, is configured to lyophilize the substance(s) and maintain a controlled environment around the substance(s) after the lyophilization process.

The alteration of an environmental factor is often within ranges typically achievable by commercially available lyophilizers. A number of the environmental factors are reduced to a negligible level, such that further reduction would not offer significant additional benefit in lyophilization or preservation of samples. One such factor is humidity wherein it is desirable to bring the relative water vapor content of the air close to zero percent. Humidity can be expressed as a relative value compared with maximum saturation under given conditions or an absolute value measured in grams of water per cubic meter. A 1% relative humidity at 25° C. is equivalent to an absolute humidity of 0.23 $g/m^3$ and a relative humidity of 5% at 25° C. is equivalent to 1.15 $g/m^3$.

For example, relative humidity within a lyophilizer may be reduced to approximately 0% (undetectable with conventional equipment) or less than 1%. Absolute humidity can be reduced to ≤0.23 $g/m^3$. A controlled environment can also include altering the amount of an inert gas, such as nitrogen, to a greater or lesser proportion than present in the ambient atmosphere. A controlled environment can thus be characterized by any or all of reduced atmospheric pressure (vacuum), reduced atmospheric water vapor content (humidity), increased inert gas content, or reduced atmospheric temperature; compared to the surrounding uncontrolled environment. Measurements for these altered factors are generally known, formulae for converting between relative and absolute values thereof are readily achieved. Various embodiments of the apparatus and methods of its use described herein will maintain a controlled environment around one or more lyophilized substances after the controlled environment within a lyophilizer has been replaced with an atmosphere comprising levels of factors that are less desirable for the lyophilized substance(s) than is the controlled environment.

The lyophilization nest is based in part on the insight that conventional formats for lyophilizing and then resealing substance(s) in receptacles (e.g., vials and/or multi-well plates) may result in excessive rehydration of the lyophilized substance(s) due to prolonged contact with a surrounding uncontrolled environment from the time of releasing the seal of a lyophilizer until the individual wells are resealed. Excessive hydration can reduce the activity or shelf-life of substance(s), or in some cases can even result in an exothermic and potentially dangerous reaction. This excessive contact may result from a work flow that requires the resealing process be performed at a work station located some distance away from the lyophilizer, or at later time after the release of the seal of the lyophilizer Accordingly, herein described is an apparatus for reducing, minimizing and/or avoiding potentially detrimental exposure of lyophilized substance(s) to undesirable levels of environmental factors in an uncontrolled environment, and thereby absorbing moisture. The apparatus can be used with or without conventional means of reducing rehydration of samples, such as glove boxes and dry rooms.

Exposure of lyophilized substances to undesirable levels of environmental factors in an uncontrolled environment may be avoided by utilizing a sealable lyophilization nest apparatus that preserves within the apparatus a controlled environment formed in the chamber of a sealed lyophilizer. The apparatus comprises in its interior one or more receptacles containing in a receptacle well one or more substances for lyophilization. The interior of the apparatus is in fluid communication with the controlled environment formed within the lyophilizer chamber during lyophilization and for a period of time sufficient to lyophilize the substance(s). Following lyophilization, fluid communication between the lyophilization chamber and the interior of the apparatus is then prevented by sealing the apparatus, thereby isolating the apparatus interior away from air in the chamber. The controlled environment is then altered within the chamber unsealing the chamber and allowing an uncontrolled environment inside the chamber. Though, because the interior of the apparatus is sealed, the environment in the interior of the apparatus remains favorable to maintaining the lyophilized substance(s) therein. It is noted that all of the environmental factors within the apparatus are not necessarily at the same levels as those of the controlled environment formed in the lyophilization chamber during lyophilization. For example, the temperature of the apparatus interior may change from that used during lyophilization. But, the environmental factors within the sealed apparatus interior are favorable for maintaining the lyophilized substance, such that rehydration of the lyophilized substance is restricted. The apparatus, when not in fluid communication with the environment outside of the apparatus, can maintain a favorable environment around the receptacle(s) and within the wells after release of the seal of the lyophilizer chamber until an operator is prepared for accessing the individual receptacle(s) or well(s) within such a receptacle (e.g., the individual wells).

A receptacle is a discrete and contiguous vessel for containing one or more substances. A receptacle can have one or more wells, each well for containing a substance. A receptacle with one well is referred to a single-well receptacle. A receptacle with multiple wells, such as a multi-well plate is referred to as a multi-well receptacle.

In various embodiments, the apparatus may be sealable and portable, such that the apparatus containing the receptacle(s) may be removed from the chamber of a lyophilizer and relocated to the appropriate work station (e.g., a clean room, a countertop, or a dry room) for sealing of individual receptacle(s) or individual wells therein. The apparatus is referred to herein as a lyophilization nest because it provides a temporary storage unit for any lyophilized substances therein during the period of time between the release of the lyophilizer seal and the beginning of the resealing process for receptacles containing the lyophilized substance(s).

In brief, in various embodiments substance(s) to be lyophilized are placed in one or more wells of a receptacle(s). The receptacle(s) are placed within a lyophilization nest configured to support the receptacle(s) within an interior space of the lyophilization nest. The interior space of the lyophilization nest may be in fluid communication with the exterior of the lyophilization nest through one or more vent holes extending through a surface of the lyophilization nest (e.g., a cover of the lyophilization nest) so as to allow the exchange of air between the interior and exterior of the lyophilization nest. For example, the lyophilization nest may comprise a base and a cover configured to collectively define a nest interior space. The lyophilization nest may comprise a gasket situated between the base and the cover to form an air-tight seal therebetween when the base and the cover are in a closed relationship. The base may define a bottom plate configured to support one or more receptacles within the nest interior space, and the cover may define the one or more vent holes through a top plate thereof. The vents may have corresponding sealing elements in closeable engagement with the vents configured to move between an open configuration and a closed configuration. Preferably, the sealing elements are configured as stopper-like plugs that are in sliding engagement with a vent hole, and slide between an open configuration and a closed configuration. When the vents holes of the lyophilization nest are closed, the lyophilization nest is isolated against the environmental factors exterior the lyophilization nest, thus impeding the exchange of air between the interior and exterior of the lyophilization nest. The vent holes can be closed by a mechanism operable from outside a sealed lyophilizer. For example, the sealing elements may be depressed into the closed configuration by lowering a shelf within the lyophilizer against the exterior surface of the lyophilization nest cover to thereby engage and depress the sealing elements into their respective vent holes.

The lyophilization nest containing the receptacle(s) is placed within a lyophilizer with the one or more vent holes in the open position. The lyophilization chamber is then sealed and substance(s) within the receptacle wells are lyophilized. During the lyophilization process, atmospheric factors within the lyophilizer are altered to facilitate removal of water from the substance(s). This controlled environment within the lyophilization chamber consequently penetrates the interior space of the lyophilization nest through fluid communication with the one or more vent holes. The one or more vent holes are then closed, thereby sealing the lyophilization nest to impede rehydration of the substance(s) after completion of the lyophilization process by maintaining within the lyophilization nest environmental conditions that are favorable to maintaining the lyophilized substance(s). The seal on the lyophilizer is later released and the lyophilization nest containing the receptacle(s) is removed from the chamber. The lyophilization nest may then be relocated and stored with the sample vessel positioned therein until an operator is ready to use the lyophilized substance(s) located therein or to reseal the receptacle(s) containing the lyophilized substance(s) for further storage or for sale. Various embodiments of the lyophilization nest may be utilized with a lyophilizer having a vertically movable shelf that may be repositioned while the lyophilizer is sealed. Thus, the vertically movable shelf may be lowered against the lyophilization nest to engage the sealing elements and to thereby seal the vent holes of the lyophilization nest while the controlled environment is maintained within the lyophilizer.

Various components of the lyophilization nest, the receptacle, the seal and similar components can be made using materials comprising a low moisture vapor transmission rate. Moisture vapor transmission rate is a measure of the passage of water vapor through a substance. There are a number of methods for determining the moisture vapor transmission rate of a material (e.g., numerous standard methods are described by International Organization for Standardization (ISO), American Society for Testing and Materials (ASTM), and others). In addition, materials with reported moisture vapor transmission rate values are commercially available. One ordinarily skilled in the art will understand how to calculate and/or purchase materials comprising a low moisture vapor transmission rate.

Lyophilization Nest

Figure 2:
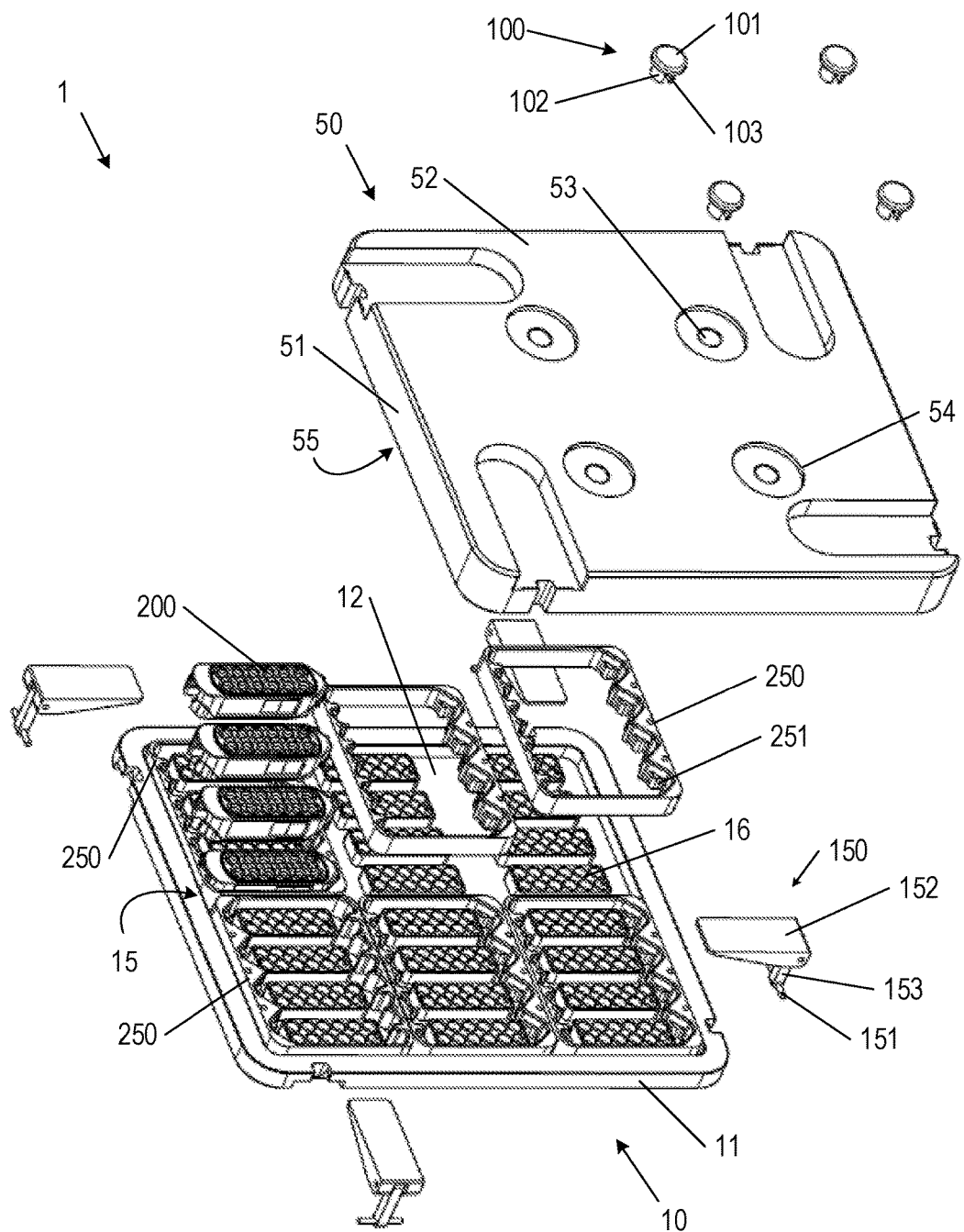
FIG. 2 shows an exploded view of a lyophilization nest according to one embodiment.

Referring now to FIG. 1, which shows an example lyophilization nest 1 in a closed configuration, the lyophilization nest 1 may define an air tight container configured to maintain a controlled environment therein. As shown in the embodiment of FIG. 1, the lyophilization nest 1 may comprise a base 10 and a cover 50 having a gasket 60 situated therebetween to form an airtight seal between the base 10 and the cover 50 when compressed between the base 10 and the cover 50. Referring briefly to FIG. 2, the cover 50 defines one or more vent holes 53 within a top plate 52 configured to selectably place an interior space of the lyophilization nest 1 in fluid communication with an atmosphere surrounding the lyophilization nest 1. As shown in the illustrated embodiment of FIG. 1, each of the one or more vent holes 53 has a corresponding sealing element 100, such as a rubber plug or other flexible plug. In the FIG. 1, each sealing element 100 is in slidable engagement with the corresponding vent hole 53 configured to engage a perimeter of the vent hole 53 and thereby form an air-tight seal therein.

Moreover, in the illustrated embodiment of FIG. 1, the lyophilization nest 1 includes one or more fasteners 150, embodied as latches, configured to selectably secure the base 10 and cover 50, and to compress the gasket 60 between the base 10 and cover 50 to form an air-tight seal therebetween. However, a variety of fasteners may be utilized to secure the base 10 and cover 50 (e.g., clamps, screws, bolts, nuts, and the like). Moreover, in various embodiments the base 10 and cover 50 may be secured via one or more hinges configured such that the base and cover may rotate around the hinge axis between an open relationship and a closed relationship. In such configurations, one or more fasteners may be utilized in conjunction with the one or more hinges such that the base 10 and cover 50 may be sealed in the closed relationship to form an air-tight seal therebetween.

In various embodiments, a plurality of bases and/or a plurality of covers may collectively define the lyophilization nest 1. As a non-limiting example, two or more covers 50 may be configured to be secured in a closed configuration with a single base 10 to define a lyophilization nest 1. Such plurality of covers may be configured to form an air-tight seal therebetween when each of the plurality of the covers 50 is engaged in a closed configuration with the base 10. For example, one or more gaskets may be positioned between each of the plurality of covers to form an air-tight seal therebetween when the lyophilization nest is in the closed configuration. As an example, two covers 50 may each be secured to opposing sides of a single base 10 via one or more hinges. The two covers thus may be configured to rotate between an open configuration in which the covers do not impede access into the interior of the base 10, and a closed configuration in which an airtight seal is formed between the two covers and the base 10.

In various embodiments, the base 10 comprises a metal material (e.g., aluminum), and the cover 50 comprises a plastic material (e.g., a high-density polyethylene material, a polyvinyl chloride material, or the like), although other materials are also contemplated. For example, each of the base 10 and cover 50 may comprise an aluminum and/or a plastic material. Each of the base 10 and the cover 50 are a material that at least substantially impedes the migration of moisture into the interior space of the lyophilization nest 1. Thus, for example, any material having a low-moisture transmission rate may be utilized (e.g., a cyclic olefin copolymer material; Topas Advanced Polymers, Inc., Florence, Ky.; cat. No. 8007S-04). As another example, other materials may be utilized in such quantities so as to provide a wall thickness of the base 10 and/or cover 50 so as to impede vapor transmission through the base and cover between the interior and exterior of the lyophilization nest 1. As a non-limiting example, each of the base 10 and/or the cover 50 may comprise a metallic material, a plastic material, a composite material, or the like.

FIG. 2, which illustrates an exploded view of the various components of the lyophilization nest 1, provides additional details of each of the various components of the lyophilization nest 1. In the illustrated embodiment of FIG. 2, the base 10 comprises a raised base edge 11 surrounding a bottom plate 12 which, collectively with a top surface of the bottom plate 12, defines a base interior 15. As shown in FIGS. 1 and 2, the base 10 may be at least substantially rectangular, although the base 10 may have any of a plurality of shapes (e.g., round, triangular, and the like). In various embodiments, the raised base edge 11 comprises a smooth sealing surface configured to engage the gasket 60 (not shown in FIG. 2) so as to provide an air-tight seal therebetween when the gasket 60 is compressed between the raised base edge 11 and a corresponding cover edge, as discussed herein.

In the illustrated embodiment of FIG. 2, the base interior 15 is configured to support a plurality of individual receptacles 200 therein. As will be described in greater detail herein, each of the plurality of receptacles 200 may define one or more substance wells each configured to hold a substance to be lyophilized. For example, each of the receptacles 200 may be a single well receptacle or a multi-well receptacle. The base interior 15 may comprise one or more receptacle receiving portions 16 therein. Each of the one or more receptacle receiving portions 16 may be integrated into the base 10. In various embodiments, the one or more receiving portions 16 may be secured to the base 10. Like the base 10, the one or more receptacle receiving portions 16 may comprise aluminum; although a plurality of alternative materials are contemplated. In various embodiments, the one or more receptacle receiving portions 16 may be configured to conduct heat away from the one or more receptacles 200 positioned therein and/or may be configured to support the one or more receptacles 200 in an upright position. Accordingly, the one or more receptacle receiving portions 16 may be configured to support and/or conform to an exterior shape of at least a bottom portion of the one or more receptacles 200 to be positioned therein to maximize a surface contact area between the receptacles 200 and the corresponding receptacle receiving portions 16. Moreover, the one or more receptacle receiving portions 16 may comprise a material having a high heat transfer coefficient (e.g., aluminum), and may be in substantial contact with the base 10 such that heat transfer between the one or more receptacle receiving portions 16 and the base 10 is maximized. Referring again to the example lyophilization nest 1 illustrated in FIG. 2, the one or more receptacle receiving portions 16 are formed from a single piece of material with the base 10. In various embodiments, the one or more receptacle receiving portions 16 may be removably secured to the base 10.

In the illustrated embodiment of FIG. 2, the lyophilization nest 1 additionally comprises a cover 50 having a shape corresponding to the base 10. In the illustrated embodiment, the cover 50 has a rectangular shape corresponding to the base 10. However, alternative shapes are contemplated (e.g., round, triangular, and the like).

Figure 3:
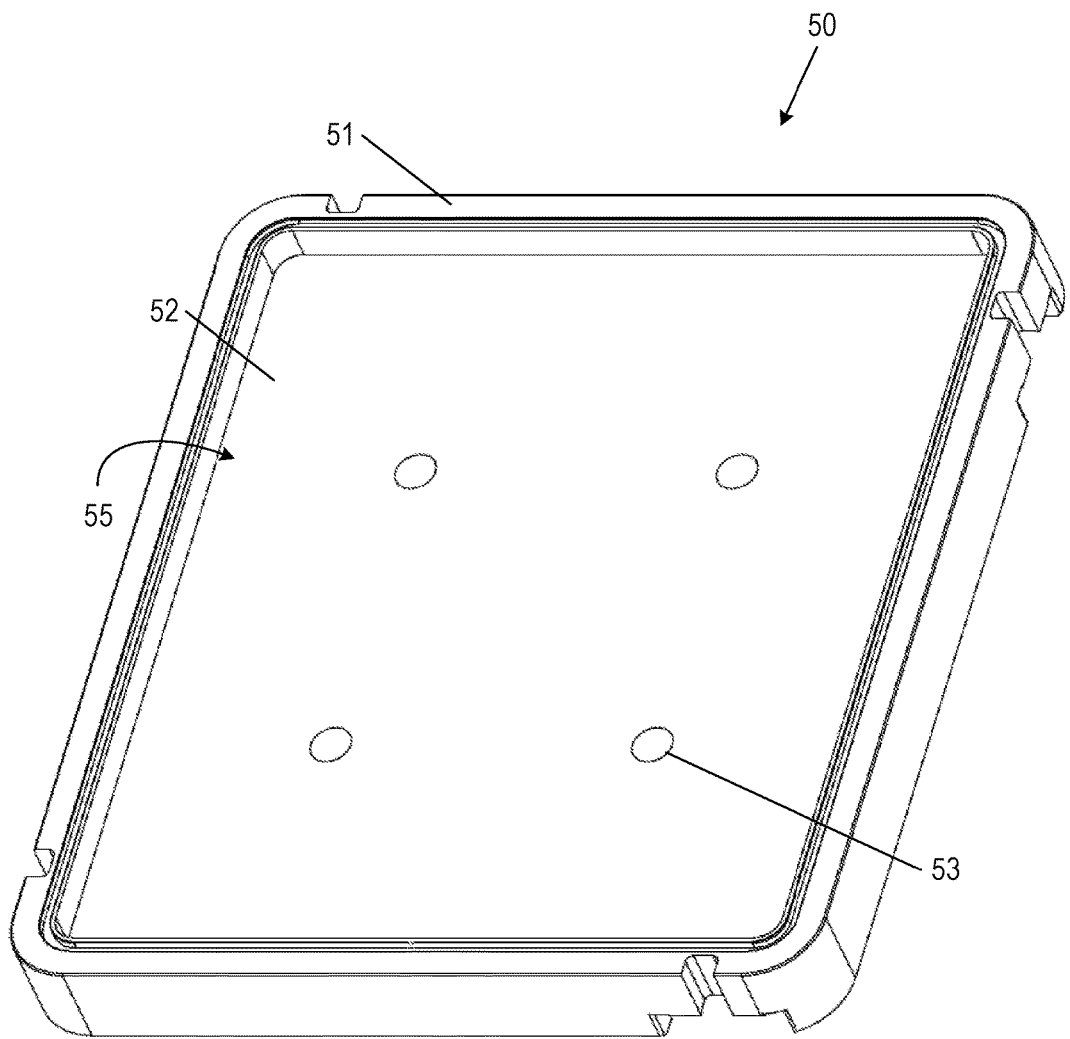
FIG. 3 shows a bottom perspective view of a lyophilization nest cover according to one embodiment.

As shown in FIG. 3, which illustrates a bottom view of a cover 50 according to various embodiments, the cover 50 has a cover edge 51 around the perimeter of a top plate 52 and extending away from the top plate 52 to define a cover interior 55. In the illustrated embodiment, the cover edge 51 comprises an at least substantially smooth surface configured to form an air-tight seal with the gasket 60 (not shown in FIG. 3) and the corresponding base edge 11 (FIG. 2) when the gasket is compressed between the cover edge 51 and base edge 11. Moreover, in various embodiments, the gasket 60 may be secured to one of the cover 50 or the base 10 (FIG. 2) such that a sealing portion of the gasket 60 is located between the base edge 11 and the cover edge 51.

Although the illustrated embodiments of FIGS. 1-3 show the base edge 11 and cover edge 51 as comprising substantially flat surfaces configured to compress a gasket 60 therebetween to provide an air-tight seal, various embodiments may comprise other configurations for providing an air-tight seal between various components of the lyophilization nest 1. As a non-limiting example, the base edge 11 and cover edge 51 may have an interlocking configuration such that the surfaces of the base edge 11 and cover edge 51 may comprise corresponding features such that the base edge 11 and the cover edge 51 may interlock when the lyophilization nest 1 is in the closed configuration. For example, the base edge 11 and cover edge 51 may have a tongue-and-groove configuration, such that at least one of the base edge 11 and the cover edge 51 may comprise a tab configured to engage a corresponding groove on the other to form a seal therebetween. In various embodiments, a gasket may be provided between the base edge 11 and cover edge 51 (e.g., within the groove and/or on the tab).

As shown in FIGS. 2 and 3, the cover 50 may define one or more vent holes 53 extending through the top plate 52 from a top surface to an interior surface of the top plate 52 such that the interior volume of the cover interior 55 is in fluid communication with air surrounding the lyophilization nest 1 through a vent hole 53. Fluid communication through a vent hole 53 permits the exchange of air between the interior space of the lyophilization nest 1 and the exterior of the lyophilization nest 1. In various embodiments, each of the one or more vent holes 53 may correspond to an individual compartment within the lyophilization nest 1 that, when the cover 50 is secured with the base 10, is isolated from the other individual compartment(s). However, in various embodiments, each of the one or more vent holes 53 may each place a single interior space of the lyophilization nest in fluid communication with the air surrounding the lyophilization nest 1. As shown in FIG. 2, each of the vent holes 53 may have a corresponding sealing element 100 (e.g., a flap, a rubber plug or other flexible plug) in slidable engagement with the corresponding vent hole. The sealing elements 100 are configured to engage the perimeter of the vent hole 53 and thereby form an air-tight seal within the vent hole 53, which isolates the interior space of the lyophilization nest 1 (collectively defined by the base interior 15 and the cover interior 55) from the air surrounding the lyophilization nest 1 exterior (external to the base 10 and the cover 50). As shown in FIG. 2, at least a portion of the sealing element 100 may be positioned external to the sealable lyophilization nest 1, and may be configured to be depressed at least partially into the top plate 52 to form an air tight seal in the corresponding vent hole 53. Moreover, as shown in FIGS. 1 and 2, the top plate 52 may define an indentation 54 surrounding each of the one or more vent holes 53. In the illustrated embodiment of FIGS. 1 and 2, the indentation 54 may have a uniform depth across the entire indentation 54 thus defining an indentation surface on the bottom of the indentation 54, and may be configured such that a portion of the sealing element 100 is placed against the indentation surface when sealed within the corresponding vent hole 53. Moreover, the indentation 54 may have a depth such that a top surface of the sealing element 100 is at least substantially aligned with the exterior surface of the top plate 52 when sealed within the corresponding vent hole 53.

Although the illustrated embodiment of FIGS. 1-3 show the one or more vent holes 53 as extending through a top plate 52 of a cover, various embodiments of the lyophilization nest 1 have vent holes 53 extending through other portions of the lyophilization nest 1. For example, the one or more vent holes 53 may extend through a side of the lyophilization nest 1, and/or through the base 10. In various embodiments, a lyophilizer may comprise a lyophilization nest sealing system configured to engage the one or more sealing elements and move the one or more sealing elements to the closed configuration. In various embodiments, the lyophilization nest sealing system may be configured to be operated while the lyophilizer is sealed.

FIGS. 4A-4C illustrate various positions of the sealing element 100 operable between an open configuration (FIGS. 4A & 4B) and a closed configuration (FIG. 4C) with respect to a corresponding vent hole 53. FIGS. 4A-4C illustrate the optional indentation 54, in which is vent hole 53. As shown in FIGS. 4A and 4B, each of the sealing elements 100 may define a sealing cap 101, a body portion 102, and a vent slot 103 configured such that the interior space of the lyophilization nest 1 may remain in fluid communication with the air surrounding the lyophilization nest 1 through the one or more vent holes 53 with the corresponding sealing element 100 placed loosely therein. In various embodiments, the sealing cap 101 may define a top surface of the sealing element 100. As shown in FIGS. 4A-4C, the sealing cap 101 is illustrated as a round element having a flat top surface and a flat bottom surface. The sealing cap 101 is secured to a body portion 102 of the sealing element 100. As shown in FIGS. 4A-4B, a top portion of the body portion 102 of the sealing element is secured to a bottom surface of the sealing cap 101. In various embodiments, the edges of the sealing cap 101 may extend beyond the perimeter of the body portion 102, such that a portion of the bottom surface of the sealing cap 101 is configured to be in sealing contact with the top surface of the top plate 52 when the sealing element 100 is inserted into a corresponding vent hole 53 in the closed configuration. With reference to FIGS. 4A-4B, as a specific example, the body portion 102 and sealing cap 101 of the sealing element 100 may be concentric and circular in shape, wherein the diameter of the sealing cap 101 is larger than the diameter of the body portion 102.

Moreover, as shown in FIGS. 4A-4B, the sealing element 100 may have a vent slot 103 extending through at least a portion of the body portion 102. For example, as shown in FIGS. 4A and 4B, the vent slot 103 may extend from a bottom portion of the body portion 102 toward a top portion of the body portion 102 and terminate between the bottom portion and the top portion of the body portion 102. In various embodiments, the vent slot 103 may extend across the entire diameter of the body portion 102. Moreover, in various embodiments, the sealing element 100 may comprise a single piece of flexible material. Thus, with the sealing element 100 placed in an open configuration in which the sealing element 100 is placed loosely within a corresponding vent hole 53 such that a portion of the vent slot 103 is located external to the top surface of cover 50 as shown in FIG. 4B, the interior space of the lyophilization nest 1 remains in fluid communication with the air surrounding the exterior of the lyophilization nest 1. Once the one or more sealing elements 100 are pressed into the corresponding vent holes 53 in a closed configuration, (FIG. 4C) such that the bottom surface of the sealing cap 101 is in sealing contact with a top surface of the cover 50, the interior space of the lyophilization nest 1 is sealed from the exterior of the lyophilization nest and the interior space of the lyophilization nest is no longer in fluid communication with the exterior of the lyophilization nest. In various embodiments, the one or more sealing elements 100 may comprise a rubber material, however a plurality of resilient and/or flexible materials are contemplated (preferably resilient and/or flexible materials having a low vapor transmission rate). Moreover, the one or more sealing elements 100 may be configured to be operated while the lyophilization nest 1 is located within a lyophilizer For example, as will be described in greater detail herein, the one or more sealing elements 100 may be configured to be depressed into a sealed position within the corresponding vent holes 53 by moving a vertically movable shelf or other actuated element capable of an automated movement within the lyophilizer toward the exterior surface of the lyophilization nest 1 (e.g., a downward movement toward the cover 50) to engage the one or more sealing elements 100 and thereby alter the sealing elements and the corresponding vent holes 53 from the open configuration to the closed configuration.

Figure 5:
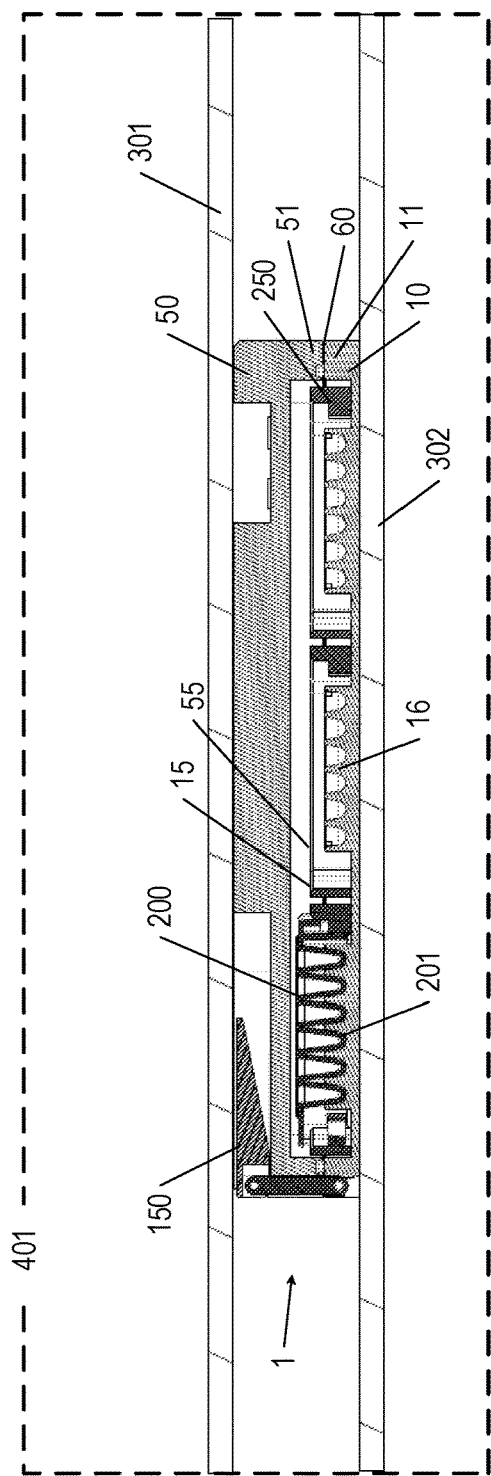
FIG. 5 shows a cross-sectional view of a lyophilization nest having a receptacle positioned therein according to one embodiment and with a top shelf and a bottom shelf in contact with the external surfaces of the cover and the base.

FIG. 5 illustrates a cross-sectional view of a lyophilization nest 1 in a closed and sealed configuration between a top shelf 301 and a bottom shelf 302 within a chamber 401 of a lyophilizer. As shown in FIG. 5, when the cover 50 is positioned such that the cover edge 51 is aligned with the base edge 11, the base interior 15 and cover interior 55 form the interior space of the lyophilization nest 1. In the illustrated embodiment of FIGS. 1, 2, and 5, the lyophilization nest 1 additionally comprises one or more fasteners 150 configured to secure the cover 50 relative to the base 10, and thereby maintain an air-tight seal therebetween. As exemplified in FIG. 2, the one or more fasteners 150 each comprise a base pin 151, a cam lever 152 and a link arm 153, though a number of fasteners can be used to secure the cover 50 to the base 10. The fasteners are configured to selectively compress the gasket 60 between cover 50 and base 10 by pressing the cover 50 toward the base 10.

Moreover, as shown in FIG. 5, the one or more receptacle receiving portions 16 comprise features for supporting and/or conforming to at least a bottom end of the receptacle 200 to be received therein. In the illustrated example of FIG. 5, the receptacle receiving portions 16 each comprise a plurality of receptacle well receiving features having a shape conforming to the exterior shape of wells 201 formed within the receptacle 200. For example, for receptacle wells 201 having a hemispherical shaped exterior, the receptacle well receiving features may have a corresponding hemispherical shape. Such corresponding shape may maximize the surface contact area of each of the one or more wells 201 in contact with the receptacle receiving portions 16 so as to maximize conductive heat transfer between a substance located within each of the one or more wells 201 and the base 10.

In the illustrated embodiment of FIG. 2, the lyophilization nest 1 is additionally configured to support one or more receptacle frames 250 each having one or more receptacle support portions 251. As shown in FIG. 2, each of the one or more receptacle frames 250 are configured to support one or more receptacles 200 therein, and thereby facilitate placement and removal of the one or more receptacles 200 within the lyophilization nest 1. As shown in the illustrated embodiment of FIG. 2, the one or more receptacle frames 250 may be configured to be situated on a top surface of the bottom plate 12 and positioned around the one or more receptacle receiving portions 16 and to extend above a top surface of the base edge 11 when positioned within the base 10. Accordingly, the perimeter of the one or more receptacle frames 250 may thereby provide a positioning guide for ensuring the cover 50 is appropriately positioned relative to the base 10 such that an air-tight seal may be formed therebetween. However, in various embodiments, at least one of the cover 50 and/or the base 10 may comprise one or more extrusions extending beyond a surface of the corresponding edges 11 and 51 to provide a positioning member for positioning the cover 50 relative to the base 10. Moreover, in various embodiments each of the one or more receptacle frames 250 may comprise aluminum, although any of a variety of rigid materials may be utilized (e.g., plastic, other metals, composites, and the like).

Figure 6A:
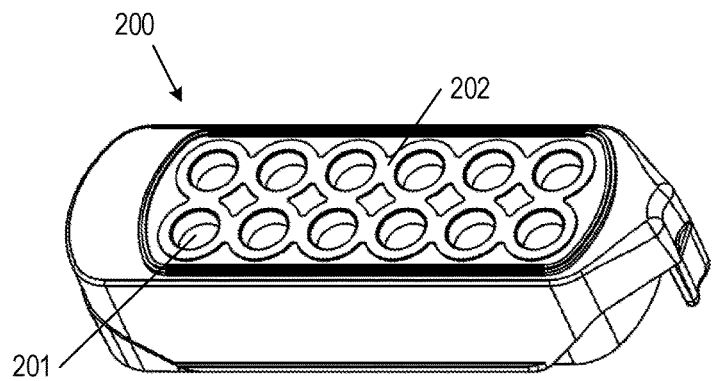
FIGS. 6A-6C show various views of a receptacle according to one embodiment.
Figure 6B:
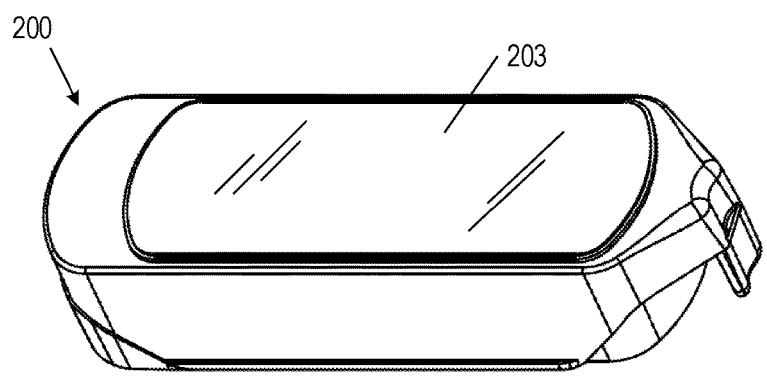
Figure 6C:
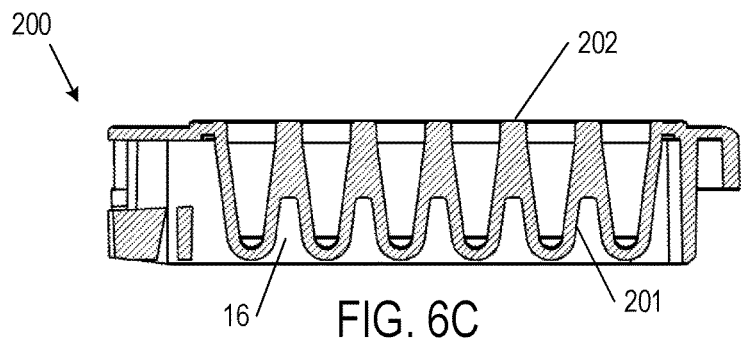

FIGS. 6A-6C illustrate a receptacle 200 that may be positioned within a lyophilization nest 1 according to various embodiments. As shown in FIGS. 6A & 6C, each of the one or more receptacles 200 may define one or more wells 201 configured to receive a substance to be lyophilized. For example, each of the one or more receptacles 200 may comprise a single well or multiple wells. Each of the one or more receptacles 200 may comprise a low vapor transmission rate material configured to impede migration of water vapor through the material (e.g., a cyclic olefin copolymer), although other materials may be used (e.g., polypropylene). Moreover, each of the one or more receptacles may have a sealable upper surface 202 configured such that a seal (e.g., an adhesive low moisture vapor transmission material that secures to the sealable upper surface 202 of the receptacle 200) may be applied thereto and sealed such that each of the one or more wells are individually sealed and isolated from an uncontrolled environment external to the sealed receptacle and/or well. For example, as shown in FIG. 6B, a seal 203 may be secured and sealed to the top of the receptacle 200 and around each of the one or more wells 201 (not shown in this Figure). In a preferred embodiment the seal 203 is a low moisture vapor transmission film such as a laminate structure comprising a layer of aluminum foil, though the seal can be made from other materials. Each of the one or more wells 201 may be accessed individually by piercing through the seal 203, by peeling the seal 203 off of the sealable upper surface 202 or by otherwise removing the seal from above one of the wells 201 to gain access to that well. Removing the seal 203 (e.g., piercing) to gain access to the lyophilized substance in the below well 201 puts that well in fluid communication with the air external the receptacle 200. Lyophilized substance within a well 201 wherein the seal 203 has been removed can then be purposely rehydrated or otherwise manipulated according to a desired use for the reconstituted reagent. In a sealed multi-well receptacle 200, lyophilized substances in other of the one or more wells 201 wherein the above seal 203 has not been pierced or removed can be stored for later use. As an additional example, each of the one or more wells 201 may have an associated sealing cap configured to be secured within the well to provide an air-tight seal around the perimeter of the well.

As shown in FIG. 6C, which is a cross-section of a row of wells 201 of a receptacle 200 according to various embodiments, each of the plurality of wells may have an at least substantially hemispherical shaped bottom interior surface. Moreover, as shown in FIG. 6C, the exterior of each of the plurality of wells 201 may have a corresponding at least substantially hemispherical surface. As described herein, at least the bottom end of the exterior surface of each of the plurality of wells 201 may be configured to conform with a receptacle well receiving feature of a receptacle receiving portion 16 of a lyophilization nest 1. As previously noted, such corresponding features may maximize surface area contact between the well 201 and the receptacle receiving portion 16 so as to facilitate heat transfer away from the substance positioned within the well 201.

Substances that can be lyophilized by the apparatus and methods for its use include, for example, pure chemicals, chemical mixtures, biologic samples, such as cells, cell extracts or tissues, biological agents, such as nucleic acids, enzymes, antibodies and other proteins, labels, such as fluorophores, and combinations thereof. Additional examples of substances that may be lyophilized also include various reaction mixes for performing specific reactions, such as for performing Polymerase Chain Reactions (PCR), transcription mediated amplification, nucleic acid or protein capture assays, and nucleic acid or protein hybridization assays.

A multi-well receptacle means a contiguous vessel that can contain at least two substances such that they can be stored and manipulated in parallel but separately. Standard formats for multi-well receptacles include 6, 24, 96, 384 or 1536 wells. The volume of each well in an example 96 well format is about 300-400 µL with a working volume of about 75-200 µL. Volumes generally vary inversely with the number of wells, typically in a range between 1 nL and 10 mL for each well, although other sizes are also contemplated. Exemplary wells can have flat bottoms, hemispherical shaped bottoms, or V-shaped bottoms, among other shapes.

As used herein, an example lyophilizer comprises a sealable enclosure defining a chamber 401 configured to support one or more sample vessels (e.g., a multi-well sample vessel) and/or one or more lyophilization nests 1 therein. The lyophilizer is configured to generate and maintain a controlled environment having conditions necessary to lyophilize one or more substance(s) located within the sample vessels within the chamber 401. Exemplary lyophilizers are configured to adjust the levels of a number of factors of the atmosphere, such as; air pressure/vacuum level, temperature, moisture content, and gas content. Preferably, lyophilizers adjust the air pressure factor of the atmosphere by lowering the pressure within the chamber 401 thereby generating a vacuum within the chamber 401. As a non-limiting example, the pressure within the chamber 401 of the lyophilizer may be lowered to 730 mTorr or less, and more preferably to 65 mTorr or less, or raised to greater than 760 mTorr. 401. Lyophilizers also, preferably, remove heat from the chamber 401 to thereby lower the temperature within the chamber 401. The lyophilizer is thereby configured to generate an atmospheric temperature within the chamber 401 in which any water within a substance will freeze and, in conjunction with an air pressure, will sublimate out of the substance. Lyophilizers also preferably alter the amount of a gas in the chamber 401, such as by increasing the amount of nitrogen in the chamber 401. For example, after the lyophilization process is complete (e.g., after substantially all of the water is removed from the substance(s)), the chamber 401 may be filled with an inert replacement gas (e.g., pure dry nitrogen gas) and thereby raise the pressure within the chamber 401 to at least substantially atmospheric pressure. For example, pure dry nitrogen gas may be introduced to the chamber 401 of the lyophilizer while maintaining the pressure within the chamber 401 below atmospheric pressure (e.g., 730 mTorr or less). However, in various embodiments, the lyophilizer may not introduce an inert gas into the chamber 401, thus maintaining a vacuum having a pressure less than 730 mTorr, and preferably less than 65 mTorr within the chamber 401 of the lyophilizer In yet other embodiments, an inert gas may be introduced to the chamber 401 of the lyophilizer to raise the pressure within the chamber 401 to atmospheric pressure (e.g., 760 mTorr) or above. The negligible humidity of the resulting controlled environment (e.g., via sublimation followed by introduction of an inert gas) facilitates lyophilization of a substance(s) and impedes rehydration of the lyophilized substance(s) after lyophilization. Such negligible humidity level may be characterized in that a further reduction in humidity would not offer a significant added benefit in impeding rehydration of the one or more lyophilized substances. Depending on the substance to be lyophilized, the levels of various environmental factors are adjusted and controlled so to lyophilize the substance. Those skilled in the art of lyophilization will readily develop and implement a set of controlled environmental conditions to achieve lyophilization of a substance of interest.

Lyophilizers can be adapted to include one or more vertically movable shelves and/or other actuated elements that may be repositioned using a user control system while the chamber 401 is sealed. Such vertically movable shelves and/or other actuated elements may be utilized to apply a pressure to the one or more sealing elements and thereby depress the sealing elements into respective vent holes in the lyophilization nest. In various embodiments, a lyophilizer may comprise a lyophilization nest sealing system configured to engage the one or more sealing elements of the lyophilization nest and move the one or more sealing elements into the closed configuration. For example, the lyophilization nest sealing system may comprise a sealing member configured to engage the one or more sealing elements and move the sealing elements to the closed configuration. Collectively, the lyophilizer and the lyophilization nest 1 define a lyophilization system.

Method of Use

Figure 7:
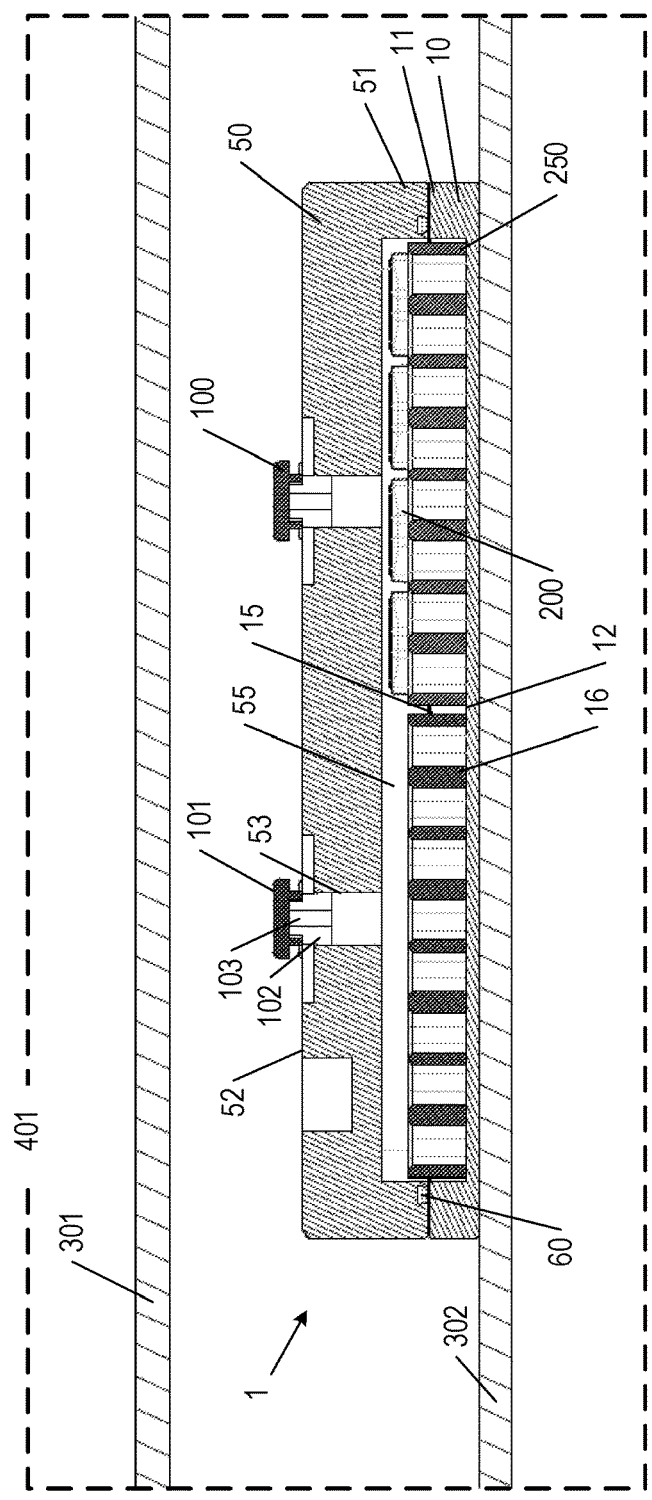
FIGS. 7-9 include cross-sectional views of a lyophilization nest in various configurations according to one embodiment, the lyophilization nest containing receptacle(s) in the interior space of the nest.
Figure 8:
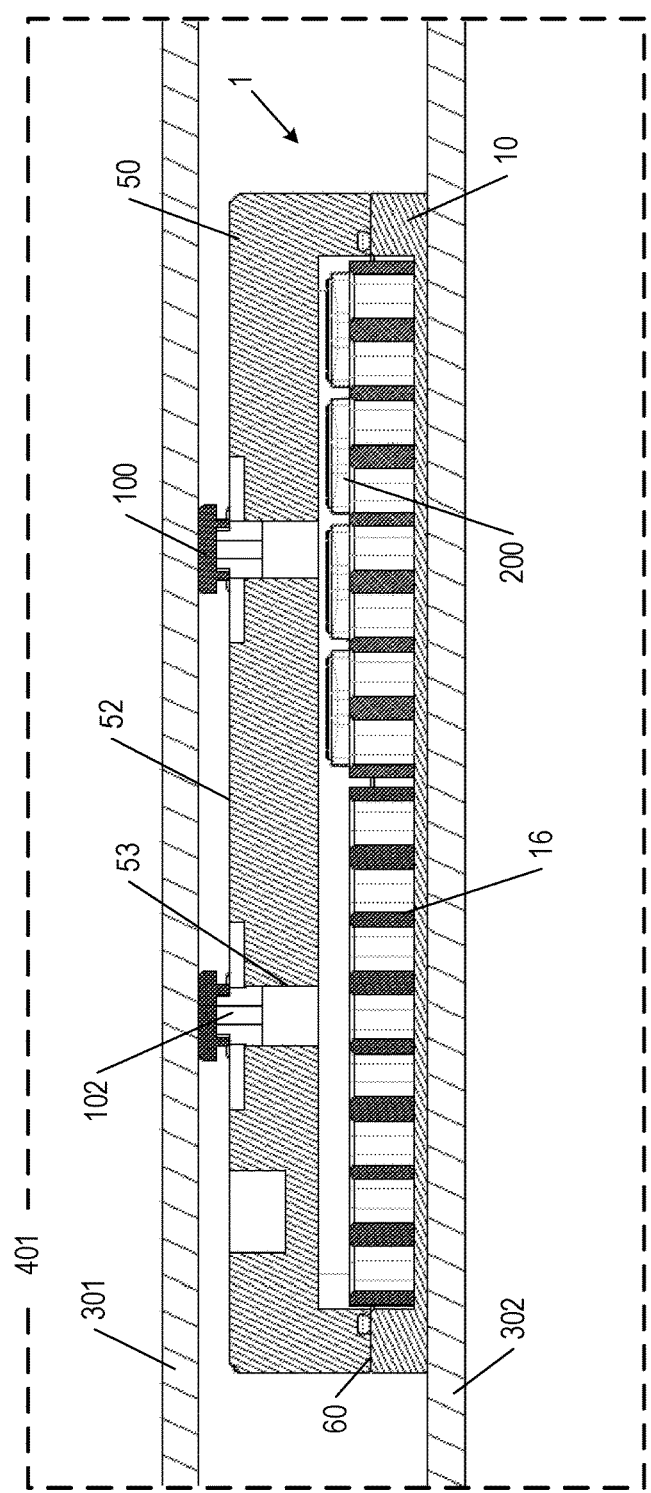
Figure 9:
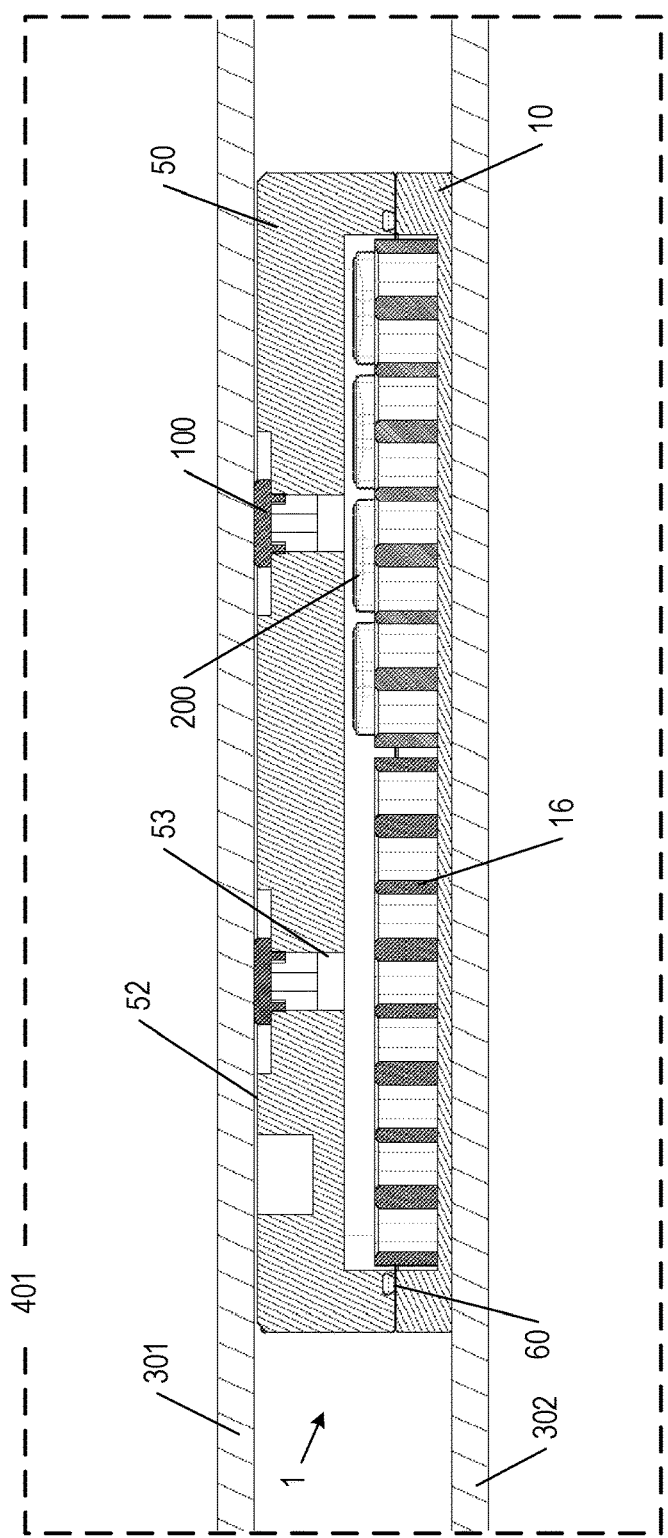

With reference to FIGS. 7-9, which illustrate various steps for sealing a lyophilization nest 1, a method of using a lyophilization nest 1 to maintain a controlled environment around one or more substances is described herein.

According to various embodiments, one or more substances to be lyophilized are placed within a receptacle 200. For example, each of a plurality of individual substances is placed within individual wells of a multi-well receptacle 200. Although the receptacles 200 are illustrated as separate from the various lyophilization nest 1 components, in various embodiments the one or more receptacles may be integrated into one of the plurality of lyophilization nest components (e.g., the base 10). The one or more receptacles 200 are positioned on a top surface of the base plate 12 and within the base interior 15. In various embodiments, each of the one or more receptacles 200 are positioned within the base interior 15 relative to a corresponding receptacle receiving portion 16. For example, for a receptacle 200 having one or more individual wells, the corresponding receptacle receiving portions 16 may comprise individual well receiving portions having an interior surface corresponding to an exterior shape of each of the one or more individual wells of the receptacle 200. Moreover, in various embodiments, each of the one or more receptacles 200 is positioned within a receptacle frame 250 before being placed within the base interior 15. For example, as shown in FIG. 2, four (4) individual receptacles 200 may be positioned within a single receptacle frame 250 which may then be placed in the interior of the base 15.

Once the one or more receptacles 200 having one or more substances to be lyophilized are placed within the base interior 15, the cover 50 is placed over the base 10 such that the base interior 15 and cover interior 55 collectively form a nest interior space having the one or more receptacles 200 positioned therein. In various embodiments, the one or more fasteners 150 (e.g., latches, not shown) are engaged with the base 10 and the cover 50 to compress the gasket 60 between the base edge 11 and the cover edge 51, forming an air-tight seal therebetween when the base 10 and cover 50 are in the closed relationship. However, in various embodiments, the cover 50 is placed loosely over the base 10 such that the air-tight seal may be formed while the lyophilization nest 1 is positioned within the chamber 401 of the lyophilizer.

As shown in FIG. 7, one or more sealing elements 100 (e.g., rubber plugs) are placed loosely within corresponding vent holes 53 in the cover 50 such that the interior space of the lyophilization nest 1 remains in fluid communication with the environmental conditions around the exterior of the lyophilization nest (e.g., conditions within a chamber 401 of a lyophilizer) via the one or more vent holes 53. As described herein, with the one or more sealing elements 100 placed loosely within corresponding vent holes 53 such that the sealing elements 100 are in an open configuration and the interior space of the lyophilization nest 1 is in fluid communication with the exterior of the lyophilization nest 1 via the one or more vent holes 53, the sealing elements 100 are in slidable engagement with the corresponding vent holes 53 such that the sealing elements 100 may be depressed into the closed configuration to seal the vent holes 53.

The assembled lyophilization nest 1 is then placed within a lyophilizer having a sealable enclosure defining a chamber 401 having a seal configured to maintain therein an environment for lyophilizing one or more substances, and having at least one vertically movable shelf configured for an automated movement and operable from the exterior of the lyophilizer while the chamber 401 is sealed. For example, the lyophilization nest 1 is placed on a bottom shelf 302 within the chamber 401 below at least one top shelf 301. A controlled environment is formed within the chamber 401. The interior space of the lyophilization nest 1 is in fluid communication with the chamber 401 and thus each of the one or more substances is in contact with the controlled environment and is lyophilized After the one or more substances are lyophilized, and while the controlled environment remains within the chamber 401, each of the one or more vent holes 53 is sealed by depressing the corresponding sealing elements 100 into the vent holes 53 of the top plate 52 of the cover 50. One or more of the factors of the controlled environment within the chamber 401 is then maintained in the interior space of the lyophilization nest 1 while the chamber 401 is unsealed allowing the environment in the chamber to change to include environmental factor levels that are unfavorable to the lyophilized substance(s). FIGS. 8-9 illustrate one embodiment for sealing a lyophilization nest 1 in a chamber 401 so that the controlled environment in the chamber 401 can be replaced with ambient air while the controlled environment is maintained within the interior of the sealed lyophilization nest 1.

As shown in FIGS. 8-9, a top shelf 301 within the chamber 401 is moved to engage the one or more sealing elements 100 and to contact the exterior surface of the top plate 52 of the cover 50 such that each of the sealing elements 100 are depressed into the corresponding vent holes 53 to form an air-tight seal therein and thereby close the vent holes 53 to seal the interior space of the lyophilization nest 1. As a non-limiting example, a vertically movable top shelf 301 may be lowered onto the exterior surface of the top plate 52 of the cover 50 while the sealing elements 100 are loosely positioned within the corresponding vent holes allowing for fluid communication from the lyophilizer chamber to the interior space of the lyophilization nest via exposed vent slot 103 and vent hole 53 (FIGS. 7 & 8). Top shelf 301 vertically lowers further onto the exterior surface of the top plate 52 of the cover 50 and fully depresses the sealing elements into the corresponding vent holes 53, as shown in FIG. 9. As another non-limiting example, a bottom shelf 302 having the lyophilization nest 1 positioned thereon may be moved upward such that the exterior surface of the lyophilization nest 1 contacts a surface located above the lyophilization nest 1, such that the sealing elements are depressed into the corresponding vent holes 53. As another non-limiting example, a lyophilization nest sealing system may engage the one or more sealing elements 100 and move the sealing elements into the closed configuration. Referring again to FIGS. 4B-4C, the sealing element 100 may be depressed into a corresponding vent hole 53 from a loose position as shown in FIG. 4B to a sealed position as shown in FIG. 4C in which a portion of the sealing element 100 is in contact with a bottom indentation surface of a corresponding indentation 54 and a top surface of the sealing element 100 is at least substantially aligned with the exterior surface of the top plate 52. Particularly when sealing the one or more sealing elements 100 within the corresponding vent holes 53 while a vacuum is present within the chamber 401 of the lyophilizer, depressing the one or more sealing elements 100 until the top surface of the one or more sealing elements 100 substantially aligns with the exterior surface of the top plate 52 may prevent the one or more sealing elements 100 from becoming secured to a smooth surface of the top shelf 301.

In various embodiments, an air-tight seal may be formed between the cover 50 and the base 10 while the cover 50 and the base 10 are in a closed relationship by depressing the cover 50 against the base 10 and thereby compressing the gasket 60 therebetween. As a non-limiting example, when a vacuum is formed within the chamber 401 of the lyophilizer, the air-tight seal between the base 10 and the cover 50 may be formed while the lyophilization nest 1 is positioned within the chamber 401. After the vacuum is released within the chamber 401, negative pressure within the interior space of the lyophilization nest 1 may maintain the air-tight seal between the base 10 and the cover 50.

Once the interior space of the lyophilization nest 1 is isolated from the surrounding environment within the chamber 401 by an air-tight seal within each of the plurality of vent holes 53 and between the cover 50 and the base 10, the environment within the chamber 401 of the lyophilizer can be replaced with air that is unfavorable to lyophilization (e.g., high moisture content) by allowing air exterior to the lyophilization chamber 401 to flood into the chamber 401. For example, an access door and/or a vent of the chamber 401 may be opened and thereby the environment within the chamber 401 is replaced by the environment from the space external to the lyophilizer. Thus, the gaseous composition, air pressure, temperature and/or humidity level within the chamber 401 may change to become equivalent to the environment surrounding the lyophilizer (e.g., the environment of the room in which the lyophilizer is placed). Because the interior space of the lyophilization nest 1 is isolated from the surrounding environment, a controlled environment within the lyophilization nest 1 is maintained.

As a non-limiting example, a vacuum may be maintained within the lyophilization nest 1 for at least 4 hours. As another non-limiting example, a flooded nitrogen environment may be maintained within the lyophilization nest 1 for at least 8 hours in various embodiments. Absolute humidity within the interior space of the lyophilization nest 1 may remain at ≤0.23 g/m³ for at least four hours.

Lyophilized substance(s) in the lyophilization nest 1 are preferably sealed directly in the receptacle 200 for later use, which requires that the lyophilization chamber 401 is opened, the sealed lyophilization nest 1 from therein is removed and located to a processing station, and the receptacle(s) 200 sealed. From the time that the chamber 401 door is opened, during removal of the lyophilization nest 1 from the chamber 401 to a processing station, and up until the time just prior to unsealing the lyophilization nest 1 for access to the receptacle(s) 200 therein, the environmental conditions in the interior of the lyophilization nest 1 are favorable to maintaining the lyophilized substance(s). To access the one or more receptacles 200 and the lyophilized substance(s) stored therein, the cover 50 is removed from the base 10, and the receptacles 200 removed from the lyophilization nest 1 and sealed for storage and later use or otherwise additionally processed. Thus, the lyophilized substance(s) within the lyophilization nest 1 have a reduced exposure time to an uncontrolled environment, thereby impeding absorption of water and thereby maintaining the integrity of the lyophilized substance(s).

When lyophilizing large batches of substances in a single lyophilization treatment, a plurality of lyophilization nests 1 are used to maintain a controlled environment within the interior of each lyophilization nest 1 and surrounding the lyophilized substances therein, as is described herein. To accommodate a plurality of lyophilization nests 1 in a chamber 401 the chamber may include three or more shelves. In a configuration wherein the chamber 401 includes three or more shelves, there is one true top shelf 301, one true bottom shelf 302, and at least one middle shelf. In this configuration, each middle shelf can function as both a top shelf 301 wherein it depresses a sealing element 100 on the top surface of a below lyophilization nest 1, and a bottom shelf 302 wherein a lyophilization nest 1 rests atop its top surface. Here, the plurality of lyophilization nests 1 sitting on a number of the three or more shelves can be sealed in an accordion-like action between the three or more shelves within the chamber 401. Other configurations are also useful for using a plurality of lyophilization nests 1 in a chamber 401. Once the plurality of lyophilization nests 1 are sealed, the lyophilizer is opened allowing air to flow into the chamber 401. A controlled environment is maintained in the interior space of the sealed lyophilization nests 1 while these lyophilization nests 1 are transferred to a station for further processing of the one or more receptacles 200 therein. A subset (e.g., 1 or less than all) of the plurality of sealed lyophilization nests 1 is then unsealed for processing of the receptacle(s) 200 therein. For example, one or more of the plurality of lyophilization nests 1 are unsealed by removing the latch 150 and separating the cover 50 from the base 10. Receptacle(s) 200 are covered with a seal 203 for storage and later use. An additional subset of the plurality of lyophilization nests 1 is then unsealed and subsequently processed. In this example the plurality of sealed lyophilization nests 1 used for lyophilizing a large batch of substances maintained a controlled environment surrounding the lyophilized substances in the interior space of each of the plurality of lyophilization nests 1 during the introduction of unfavorable environmental factors into the chamber 401 of the lyophilizer, during transportation of the plurality of sealed lyophilization nests 1 from the lyophilizer to the subsequent processing station, and while in the succession for subsequent processing.

As described, after releasing the seal on the lyophilization nest 1, lyophilized substance(s) can be used as is or the receptacle 200 can be sealed for storage and later use of the one or more lyophilized substances contained in its one or more wells 201. Resealing may not remove ambient air present in the one or more wells 201 of the receptacle 200, but such process isolates the substance(s) from prolonged contact with the unfavorable environmental factors, and thus greatly improves storage of the lyophilized substance(s). A receptacle 200 can be sealed by removing the receptacle from the lyophilization nest 1, and by applying and adhering a seal 203 (e.g. a low moisture vapor transmission film, such as, a laminate structure comprising a layer of aluminum foil) over the open face of the one or more wells 201 so as to form an air tight seal between each of the wells of the receptacle and the external surrounding air. Receptacles 200 comprising more than one well are preferably sealed with a seal 203 so that each well is individually enclosed, and so that the seal on each well to be broken independently without exposing the remaining wells to unfavorable environmental conditions.

Conclusion

Many modifications and other embodiments of the lyophilization nest set forth herein will come to mind to one skilled in the art to which the apparatus and the methods of its use pertain, in response to having the benefit of the teachings presented in the foregoing descriptions and the associated drawings. Therefore, it is to be understood that the lyophilization nest and methods for its use are not to be limited to the specific embodiments disclosed and that modifications and other embodiments are intended to be included within the scope of the appended claims. Although specific terms are employed herein, they are used in a generic and descriptive sense only and not for purposes of limitation.

I claim:

1. A lyophilization nest for preparing lyophilized substances, the nest comprising:
    a base comprising a bottom plate having a base edge extending upwardly from a perimeter thereof, the bottom plate having a top surface adapted to support a plurality of receptacles thereon;
    a cover comprising a top plate having a cover edge extending downwardly from a perimeter thereof, the top plate having one or more vent holes extending therethrough;
    an interior space defined by the base and the cover when the base and the cover are in a closed relationship, the interior space being sized to accommodate the receptacles;
    a gasket situated between the base edge and the cover edge when the base and the cover are in the closed relationship, the gasket forming an air tight seal when compressed between the base edge and the cover edge; and
    one or more sealing elements, each of the sealing elements being in closeable engagement with a corresponding one of the vent holes, such that the sealing elements and the corresponding vent holes are operable between:
        an open configuration in which the positions of the sealing elements relative to the corresponding vent holes permit fluid communication between the interior space and air external to the nest when the base and the cover are in the closed relationship; and
        a closed configuration in which the positions of the sealing elements relative to the corresponding vent holes do not permit fluid communication between the interior space and air external to the nest when the base and the cover are in the closed relationship, such that the interior space is sealed off to air external to the nest when the base and the cover are in the closed relationship.

2. The lyophilization nest of claim 1, further comprising one or more fasteners for securing the cover to the base, the fasteners being configured to compress the gasket between the base edge and the cover edge to form the air tight seal when the base and the cover are in the closed relationship, wherein the fasteners comprise one or more latches or wherein at least one of the fasteners comprises a base pin, a cam lever and a link arm.

3. The lyophilization nest of claim 1, wherein the base comprises aluminum; and/or wherein the top surface of the bottom plate comprises one or more receptacle receiving portions formed therein, each of the receptacle receiving portions having features that conform to at least a bottom end of the receptacles to be received thereon and are constructed to conduct heat between the base and the receptacles supported thereon, wherein: each of the receptacles comprises a plurality of lyophilization wells; and each of the receptacle receiving portions comprises a plurality of well receiving features conforming to the shapes of at least the bottom ends of the of lyophilization wells of the corresponding receptacle.

4. The lyophilization nest of claim 1, wherein:
    each of the sealing elements is a flexible plug that comprises a sealing cap and a body portion depending therefrom, the body portion being in closeable engagement with a corresponding one of the vent holes and having one or more vent slots formed therein; and
    each of the sealing elements is configured to be positioned in a corresponding one of the vent holes, such that (i) the interior space is in fluid communication with air external to the nest via the vent slots when the sealing element and the corresponding vent hole are in the open configuration; and (ii) the interior space is not in fluid communication with air external to the nest when a bottom surface of the sealing cap is in sealing contact with a top surface of the top plate when the sealing element and the corresponding vent hole are in the closed configuration, wherein the closeable engagement is a sliding engagement.

5. The lyophilization nest of claim 1, wherein the closeable engagement is a sliding engagement, a hinging engagement, a swinging engagement, or a rotary engagement.

6. The lyophilization nest claim 1, further comprising one or more receptacle frames situated on a top surface of the bottom plate, each of the receptacle frames being configured to support a plurality of receptacles, wherein each of the receptacle frames comprises aluminum.

7. A lyophilization system for lyophilizing a substance, the system comprising:
    a sealable enclosure defining a chamber;
    the lyophilization nest of claim 1 contained within the chamber, wherein the base and the cover are in the closed relationship, and wherein the interior space of the lyophilization nest contains at least one receptacle holding a substance to be lyophilized; and
    a top shelf and a bottom shelf contained within the chamber, wherein the lyophilization nest is situated on the bottom shelf, and wherein at least one of the top shelf and the bottom shelf is capable of an automated movement that causes the top shelf to engage the sealing elements, thereby altering the sealing elements and the corresponding vent holes from the open configuration to the closed configuration.

8. The lyophilization system of claim 7, wherein the top shelf is configured for automated, downward movement toward a top surface of the cover of the lyophilization nest, and/or wherein each of the receptacles is formed from a plastic material having a low moisture vapor transmission rate, and where each of the receptacles comprises a plurality of wells configured to be sealed.

9. A method for lyophilizing a substance, the method comprising the steps of:
   (a) positioning a lyophilization nest on a bottom shelf contained within a chamber of a lyophilizer, the lyophilization nest supporting one or more receptacles contained within an interior space of the lyophilization nest, at least one of the receptacles containing a substance to be lyophilized, wherein the interior space of the lyophilization nest is in fluid communication with air external to the nest through one or more vent holes extending through a top plate of a cover of the lyophilization nest, and wherein each of the vent holes has a sealing element in closeable engagement therewith;
   (b) closing the chamber containing the lyophilization nest;
   (c) creating lyophilization conditions within the chamber for a period of time sufficient for the substance contained in at least one of the receptacles to be lyophilized;
   (d) while the chamber is closed, causing at least one of the bottom shelf and a top shelf contained within the chamber to move so that the top shelf engages the sealing elements, thereby closing the vent holes so that the interior space of the lyophilization nest is sealed off to air external to the nest and the absolute humidity within the interior space of the lyophilization nest is stabilized; and
   (e) opening the chamber and removing the nest from the lyophilizer.

10. The method of claim 9, wherein the step of creating the lyophilization conditions comprises generating a vacuum and a temperature below freezing within the chamber, wherein the step of creating the lyophilization conditions comprises generating a vacuum and cycling between a first temperature below freezing and a second temperature below freezing within the chamber, each of the first and second temperatures being below the freezing temperature of the substance to be lyophilized.

11. The method of claim 9, wherein the absolute humidity within the interior space of the lyophilization nest is approximately 0.0 grams of water per cubic meter of air after step (d); or wherein the absolute humidity within the interior space of the lyophilization nest is less than 2.3 grams of water per cubic meter of air after step (d), wherein the absolute humidity within the interior space of the lyophilization nest is less than 1.15 grams of water per cubic meter of air after step (d), more preferably less than 0.23 grams of water per cubic meter of air after step (d).

12. The method of claims 9, wherein the lyophilization nest comprises a base comprising a bottom plate having a base edge extending upwardly from a perimeter thereof, the bottom plate having a top surface adapted to support a plurality of receptacles thereon;
   a cover comprising a top plate having a cover edge extending downwardly from a perimeter thereof, the top plate having one or more vent holes extending therethrough;
   an interior space defined by the base and the cover when the base and the cover are in a closed relationship, the interior space being sized to accommodate the receptacles;
   a gasket situated between the base edge and the cover edge when the base and the cover are in the closed relationship, the gasket forming an air tight seal when compressed between the base edge and the cover edge;
   one or more sealing elements, each of the sealing elements being in closeable engagement with a corresponding one of the vent holes, such that the sealing elements and the corresponding vent holes are operable between:
      an open configuration in which the positions of the sealing elements relative to the corresponding vent holes permit fluid communication between the interior space and air external to the nest when the base and the cover are in the closed relationship; and
      a closed configuration in which the positions of the sealing elements relative to the corresponding vent holes do not permit fluid communication between the interior space and air external to the nest when the base and the cover are in the closed relationship, such that the interior space is sealed off to air external to the nest when the base and the cover are in the closed relationship, and wherein the base and the cover are in the closed relationship.

13. The method of claims 9, further comprising the steps of:
   (f) after step (e), removing the lyophilization nest from the chamber;
   (g) accessing and removing the receptacles from the lyophilization nest; and
   (h) sealing the receptacles so as to form an air tight seal between each of a plurality of wells of each of the receptacles and air external to the wells of the sealed receptacles.

14. The method of claim 13, wherein steps (g) and (h) are performed in a space that is not controlled for humidity.

15. The method of claim 13, wherein step (h) comprises securing a low moisture vapor transmission film to a top surface of each of the receptacles to thereby form the airtight seal between the wells and air external to the wells of the sealed receptacles, wherein the low moisture vapor transmission film is a laminate comprising a layer of aluminum foil.

16. The method of claim 15, wherein the low moisture vapor transmission film further comprises an adhesive; or wherein the low moisture vapor transmission film further comprises a plastic liner for affixing the film to the top surface of each of the receptacles.

17. The method of claim 9, wherein, after step (e), the absolute humidity within the interior space of the lyophilization nest remains at less than 2.3 grams of water per cubic meter of air for at least four hours.

18. The method of claim 9, wherein the closeable engagement is a sliding engagement of the sealing element with the vent holes; or wherein the closeable engagement is a hinging engagement, a swinging engagement, or a rotary engagement of the sealing element with the vent holes.

* * * * *